United States Patent
Cosman et al.

(10) Patent No.: US 7,976,542 B1
(45) Date of Patent: Jul. 12, 2011

(54) ADJUSTABLE HIGH FREQUENCY ELECTRODE

(76) Inventors: Eric R. Cosman, Belmont, MA (US);
Eric R. Cosman, Jr., Belmont, MA (US)

( * ) Notice: Subject to any disclaimer, the term of this patent is extended or adjusted under 35 U.S.C. 154(b) by 721 days.

(21) Appl. No.: 11/365,843

(22) Filed: Mar. 2, 2006

(51) Int. Cl.
*A61B 18/14* (2006.01)

(52) U.S. Cl. ......................................................... 606/41

(58) Field of Classification Search .................... 606/41, 606/34, 32, 37, 45, 49
See application file for complete search history.

(56) References Cited

U.S. PATENT DOCUMENTS

| | | | |
|---|---|---|---|
| 4,483,338 A | 11/1984 | Bloom et al. | |
| 4,565,200 A | 1/1986 | Cosman | |
| 4,682,596 A | 7/1987 | Bales et al. | |
| 4,936,281 A | 6/1990 | Stasz | |
| 4,998,933 A | 3/1991 | Eggers et al. | |
| 5,178,620 A | 1/1993 | Eggers et al. | |
| 5,336,176 A * | 8/1994 | Yoon ............................... | 604/506 |
| 5,348,554 A | 9/1994 | Imran et al. | |
| 5,454,809 A | 10/1995 | Janssen | |
| 5,486,161 A | 1/1996 | Lax et al. | |
| 5,500,012 A | 3/1996 | Brucker et al. | |
| 5,520,684 A | 5/1996 | Imran | |
| 5,545,161 A | 8/1996 | Imran | |
| 5,554,110 A * | 9/1996 | Edwards et al. ................. | 604/22 |
| 5,599,346 A * | 2/1997 | Edwards et al. ................. | 606/41 |
| 5,658,278 A | 8/1997 | Imran et al. | |
| 5,688,267 A | 11/1997 | Panescu et al. | |
| 5,782,760 A | 7/1998 | Schaer | |
| 5,951,546 A | 9/1999 | Lorentzen | |
| 6,146,380 A | 11/2000 | Racz et al. | |
| 6,174,308 B1 * | 1/2001 | Goble et al. ..................... | 606/41 |
| 6,241,702 B1 | 6/2001 | Lundquist et al. | |
| 6,306,132 B1 * | 10/2001 | Moorman et al. ............... | 606/41 |
| 6,312,428 B1 * | 11/2001 | Eggers et al. .................... | 606/41 |
| 6,315,777 B1 * | 11/2001 | Comben ........................... | 606/41 |
| 6,325,799 B1 * | 12/2001 | Goble .............................. | 606/41 |
| 6,355,033 B1 * | 3/2002 | Moorman et al. ............... | 606/33 |
| 6,440,127 B2 | 8/2002 | McGovern et al. | |
| 6,447,505 B2 | 9/2002 | McGovern et al. | |
| 6,451,015 B1 * | 9/2002 | Rittman et al. .................. | 606/34 |
| 6,506,189 B1 | 1/2003 | Rittman et al. | |
| 6,517,534 B1 | 2/2003 | McGovern et al. | |
| 6,530,922 B2 * | 3/2003 | Cosman et al. .................. | 606/34 |
| 6,669,652 B2 | 12/2003 | Anderson et al. | |
| 6,692,493 B2 | 2/2004 | McGovern et al. | |
| 6,743,226 B2 | 6/2004 | Cosman | |
| 6,827,715 B2 * | 12/2004 | Francischelli et al. .......... | 606/34 |
| 7,077,842 B1 | 7/2006 | Cosman | |
| 7,104,987 B2 * | 9/2006 | Biggs et al. ...................... | 606/34 |

(Continued)

FOREIGN PATENT DOCUMENTS

WO WO 96/18349 6/1996

(Continued)

OTHER PUBLICATIONS

Cosman, et al., "Theoretical Aspects of Radiofrequency Lesions in the Dorsal Root Entry Zone", Neurosurgery, vol. 15, No. 6, pp. 945-950, (1984).

(Continued)

*Primary Examiner* — Linda C Dvorak
*Assistant Examiner* — Amanda Scott
(74) *Attorney, Agent, or Firm* — Steptoe & Johnson LLP

(57) ABSTRACT

A method and apparatus for application of an electrical signal to neural and other target tissue in the living body.

14 Claims, 6 Drawing Sheets

U.S. PATENT DOCUMENTS

| | | | |
|---|---|---|---|
| 7,306,596 B2 * | 12/2007 | Hillier et al. | 606/41 |
| 7,318,822 B2 * | 1/2008 | Darmos et al. | 606/31 |
| 7,377,918 B2 * | 5/2008 | Amoah | 606/34 |
| 7,387,626 B2 * | 6/2008 | Edwards et al. | 606/33 |
| 2005/0267459 A1 | 12/2005 | Belhe et al. | |
| 2005/0267552 A1 | 12/2005 | Conquergood et al. | |

FOREIGN PATENT DOCUMENTS

| | | |
|---|---|---|
| WO | WO 96/34571 | 11/1996 |
| WO | WO99/40859 | 8/1999 |
| WO | WO99/40860 | 8/1999 |
| WO | WO00/59394 | 12/2000 |

OTHER PUBLICATIONS

Gervais, et al., "Radio-frequency Ablation of Renal Cell Carcinoma: Early Clinical Experience[1]", Radiology, vol. 217, No. 3, pp. 665-672, (2000).

Goldberg, et al., "Tissue Ablation with Radiofrequency: Effect of Probe Size, Gauge, Duration, and Temperature on Lesion Volume", Acad. Radiol., vol. 2, No. 5, pp. 399-404, (1995).

Goldberg, et al., "Thermal Ablation Therapy for Focal Malignancy; a Unified Approach to Underlying Principles, Techniques, and Diagnostic Imaging Guidance", AJR, vol. 174, pp. 323-331, (2000).

* cited by examiner

ADJUSTABLE HIGH FREQUENCY ELECTRODE

TECHNICAL FIELD

This invention relates generally to field therapy.

BACKGROUND

High frequency generators, which are exemplified by radiofrequency (RF) generators, and related electrodes are commonly used in the treatment of pain and neurological diseases. Examples are the equipment and applications of Radionics, Inc., Burlington, Mass., such as the RFG-3C RF Lesion Generator and related electrode systems. Related information is provided in the paper by Cosman, E. R. and Cosman, B. J. entitled "Methods of Making Nervous System Lesions," in Wilkins R H, Rengachary SS (eds): Neurosurgery. New York, McGraw-Hill, Vol. III, 2490-2498, 1984, and is hereby incorporated by reference herein in its entirety. The Radionics brochures on the TIC Kit, TEW Kit, Gildenberg Stereotaxy Kit, and SMK Kit contain related information, and they are hereby incorporated by reference herein in their entirety.

U.S. patent application Ser. No. 11/355,960 entitled "Integral High Frequency Electrode" in the name of Eric R. Cosman, Sr. and Eric R. Cosman, Jr. describes a unitized high frequency electrode system with non-separable cable and injection components in various examples, and is hereby incorporated by reference herein in its entirety.

The U.S. patent entitled "Universal Lesion and Recording System" by Eric R. Cosman, U.S. Pat. No. 4,565,200, issued Jan. 21, 1986, describes a high frequency electrode system having an electrode that is adjustable with respect to an insulated cannula that thereby achieves variability in the length of the uninsulated electrode tip for both a straight electrode geometry as well as a flexible side-issue electrode tip geometry. That patent is hereby incorporated by reference herein in its entirety.

The Radionics TEW Kit is a commercial example of an implementation related to the above-mentioned U.S. Pat. No. 4,565,200. It includes an insulated metal tubing that is rigid. A separated RF electrode is inserted into the insulated metal tubing, and the uninsulated tip of the electrode emerges from the insulated tubing distal end. A straight electrode, as well as a flexible side-issue electrode, is included in the TEW Kit. Continuous variation of the exposed uninsulated tip length is achieved by varying the insertion depth of the electrode in the metal tubing cannula. The extent of uninsulated tip length is adjusted continuously and clamped by a setscrew on the proximal hub of the insulated metal tubing. One disadvantage is that the insulated metal tubing or cannula is straight. It is sometimes clinically desirable to have a permanent rigid, curved distal tip to an electrode or an insertion cannula for steering the electrode or cannula into the patient's body toward a desired target tissue. Another disadvantage is that the cannula of the TEW Kit is a metal tubing with an insulating coating fixed to the cannula and covering the cannula. This increases the overall diameter of the cannula and insulation combination. Another disadvantage is that the RF electrode which slides inside the insulated cannula is of a smaller diameter than the outside insulated cannula, which decreases the heating region of the electrode system for a given overall shaft diameter. Another disadvantage is that the insulating element is the outer metal tubing with its insulating covering. This is not flexible as compared to for example, an insulating sleeve that is made entirely of an insulating material, such as a plastic sleeve. Another disadvantage is that the TEW Kit components are complex and expensive to make. The insulated cannula is first inserted into the patient's body with an obdurating rigid stylet inserted into it. Once in place, the stylet is removed and the electrode, either straight or curved variety, is inserted into the cannula. This multi-step procedure increases surgery time and expense. Another disadvantage is that the TEW system does not have discrete, uninsulated electrode tip lengths at fixed finite values, but rather has a continuous range of tip exposures that are set by the setscrew. This requires more deliberate attention by the surgeon to set a desired tip length.

The Radionics TIC Kit includes four insulated cannulae with different tip exposures. The clinician decides before the procedure which length of tip exposure is desirable. One disadvantage is that the TIC Kit requires four different cannulae for the four available tip exposures. This makes the TIC Kit more complex and more expensive.

The U.S. patent entitled "Adjustable Transurethral Radiofrequency Ablation" by Eric R. Cosman and Francis J. McGovern, U.S. Pat. No. 6,743,226 D2, issued Jun. 1, 2004, describes an RF catheter system with an exposed electrode that comprises metal rings around the distal end of a urethral catheter. The length and configuration of unexposed electrode surfaces can be adjusted by changing the degree of insulation coverage of the metal electrode rings. In one example, this is achieved by removal of insulated bands that are placed on indiscrete positions on the rings so as to expose more electrode surface at desired positions. In another example, the degree of uninsulated electrode exposure can be changed by movement of an insulated sleeve over the ring. One disadvantage of these systems in the context of pain treatment is that the catheter is not rigid and therefore cannot be inserted into the skin and the patient's bodily tissues in a self-supported manner. Another disadvantage is that the system configuration cannot be used easily for percutaneous insertion of electrodes into the back near the spine or into the brain, or into other target tissues such as cancerous tumors, making the system poorly configured for applications of pain therapy or tumor therapy.

SUMMARY

The present invention relates to a system and method involving a high frequency electrode system that has a shaft that, in one example, is rigid enough for a self-supported penetration of skin and tissue. In one example, the electrode comprises a cannula that is adapted with a sharpened distal end for penetration through the skin and bodily tissues, for example, near the patient's spine or, for example, in tumor tissues. The cannula shaft, in one example, can comprise a metal tubing. There can be an insulative sleeve that slides over the metal tubing to insulate at least a portion of the surface of the tubing. In one example, the insulating sleeve can be made of a semi-rigid plastic material such as hard Teflon or polyethylene. The insulating sleeve can be positioned on the metal tubing of the cannula so that there is an exposed electrode tip surface of the cannula at the distal end of the cannula that is not covered by the insulative sleeve, referred to herein often as the uninsulated electrode tip. A high frequency signal that is connected to the cannula, in one example by an electrode or probe that is inserted within the cannula can be connected to the distal exposed electrode tip so that when the cannula is inserted into a target tissue the high frequency signal will be applied to the target tissue. The position of the insulating sleeve can determine the degree of unexposed electrode tip, or the size or length of the uninsulated electrode tip. The insulating sleeve can have a proximal hub. The metal cannula can also have a proximal hub. In one example, a discrete spacer can be interposed between the cannula hub and the hub of the insulative sleeve to fix the relative position of the cannula and the insulating sleeve. This determines the length of the uninsulated electrode tip. In another example, a spacer of different length can be interposed between the cannula hub and the hub of the insulative sleeve to produce a different length of unexposed electrode tip. In this way, the clinician can discretely change the degree of high frequency electrode tip exposure according to clinical needs.

One advantage is that, for example, the system with one cannula and one insulating sleeve can be used to establish different tip exposures according to the requirements of a particular clinical situation. Another advantage is that the system has a reduced number of components to achieve various tip exposures. Another advantage is that the system is simple to construct and has fewer components, thus reducing the cost of the system and reducing the complexity to inventory parts and components in the clinical setting.

In one example, the insulating sleeve can comprise a flexible and yet longitudinally rigid insulative tubing. The insulative tubing can slide in a close tolerance fit over the outer diameter of the underlying metal tubing cannula or the metal tubing of the high frequency electrodes. In one example, the high frequency cannula, or alternatively the high frequency electrode, can have a curved, semi-rigidly configured distal tip. The transversely flexible insulative sleeve, as is achievable by having a fully plastic insulating sleeve, can slide over the curved portion of the distal tip so that variable electrode tip exposures can be achieved even at the location of curvature of the underlying metal tubing. One advantage is that a single curved electrode system can have a variability or adjustability of the exposed electrode tip. In another example, a single cannula or electrode system can include a rigid metal tubular structure, and a set of insulative sleeves. The sleeves can have different lengths, so that when different sleeves are slipped over the cannula or electrode, different uninsulated electrode tip lengths are achieved. One advantage is that with a single cannula or electrode and with the addition of inexpensive set of insulative sleeves, a choice of several uninsulated tip exposures is available to the clinician.

In one aspect, a system of an adjustable electrode can be adapted for treatment of spinal nerves. In another aspect, the adjustable electrode system can be adapted for treatment of cancerous tumors. In another example, the adjustable electrode system can be used for the treatment of neural structures in the brain.

In one example, an electrode system can have an insulated portion that includes removable insulation bands. The clinician can decide upon the desired length of exposed electrode tip according to the size of the target tissue to be treated. One or more insulative bands, having discrete lengths, can be removed by the clinician prior to insertion of the electrode into the patient's body. Removal of the insulative bands provides adjustment in the length of tip exposure and therefore on the size of the uninsulated electrode tip to suit the particular target tissue size and other clinical needs.

In another aspect, a method of treating tissue with high frequency signal output can include selecting a high frequency electrode and/or cannula system to be inserted into the target tissue within the patient's body according to the clinical needs. The exposed electrode tip length and shape can be adjusted by adjustment of the insulation on the shaft of the cannula or electrode. The electrode can be inserted into the target tissue to the proper position under imaging control and monitoring. A high frequency generator that produces a high frequency signal output can be connected to the cannula and/or electrode. The high frequency signal output can be applied through the uninsulated electrode tip to the target tissue to achieve the appropriate clinical treatment.

In one aspect, an adjustable high frequency electrode system can include a rigid shaft adapted to be inserted into the target tissue of a living body, the rigid shaft having a distal end, the distal end including an uninsulated electrode tip, and an insulating covering that covers at least a portion of the rigid shaft. At least a portion of the insulating covering can be moved with respect to the rigid shaft so that the exposed surface of the uninsulated electrode tip can be adjusted. The electrode system can be configured to be connected to a high frequency generator so that a high frequency signal output from the high frequency generator can be applied to the target tissue near the uninsulated electrode tip when the rigid shaft is inserted into the living body. The rigid shaft can include a metal tubing, and the uninsulated electrode tip can include at least a portion of a distal end of the metal tubing. The metal tubing can have a sharpened tip at the distal end of the metal tubing to enable penetration of the tissue of the living body. The distal end of the metal tubing can have a curve shape. The insulating covering can include an insulating sleeve of electrically insulating material that covers at least a portion of the rigid shaft, and at least a portion of the insulating sleeve can be moved with respect to the rigid shaft to adjust the length of the uninsulated electrode tip. The insulating covering can include a removable insulative member covering at least a portion of the distal end. The rigid shaft can include a metal tubing and the uninsulated electrode tip can include a portion of a distal end of the metal tubing, and the insulating covering can include an insulating sleeve of insulating material that can be moved on the metal tubing to adjust the length of the uninsulated electrode tip. The adjustable high frequency electrode system can include a spacer that enables positioning the insulating sleeve at fixed positions on the metal tubing. The adjustable high frequency electrode system can also include a fixation clamp that enables the insulating sleeve to be fixed at adjusted positions on the metal tubing. The rigid shaft can include a metal tubing and the uninsulated electrode tip comprises a portion of the distal end of the metal tubing, and the insulating covering comprises a removable insulating member covering at least a portion of the distal end of the metal tubing.

In another aspect, a method of treating target tissue in the living body can include determining the size of a high frequency electrode needed to treat the target tissue with a high frequency signal output, selecting a high frequency electrode system having a rigid shaft adapted to be inserted into the target tissue, the distal end including an uninsulated electrode tip, and an insulating covering that covers at least a portion of the rigid shaft and at least a portion of the insulating covering can be moved with respect to the rigid shaft so that an exposed surface of the uninsulated electrode tip can be adjusted. The electrode system can be configured to be connected to a high frequency generator so that the high frequency signal output from the high frequency generator can be applied to a target tissue near the uninsulated electrode tip when the rigid shaft is inserted into a living body. The method can include adjusting the exposed surface according to the size of high frequency electrode and can include connecting the high frequency electrode system to a high frequency generator to deliver a high frequency signal output to the target tissue through the uninsulated electrode tip.

The details of one or more embodiments of the invention are set forth in the accompanying drawings and the description below. Other features, objects, and advantages of the invention will be apparent from the description and drawings, and from the claims.

DESCRIPTION OF DRAWINGS

In the drawings which constitute a part of the specification, embodiments exhibiting various forms and features hereof are set forth, specifically.

DETAILED DESCRIPTION

Figure 1:
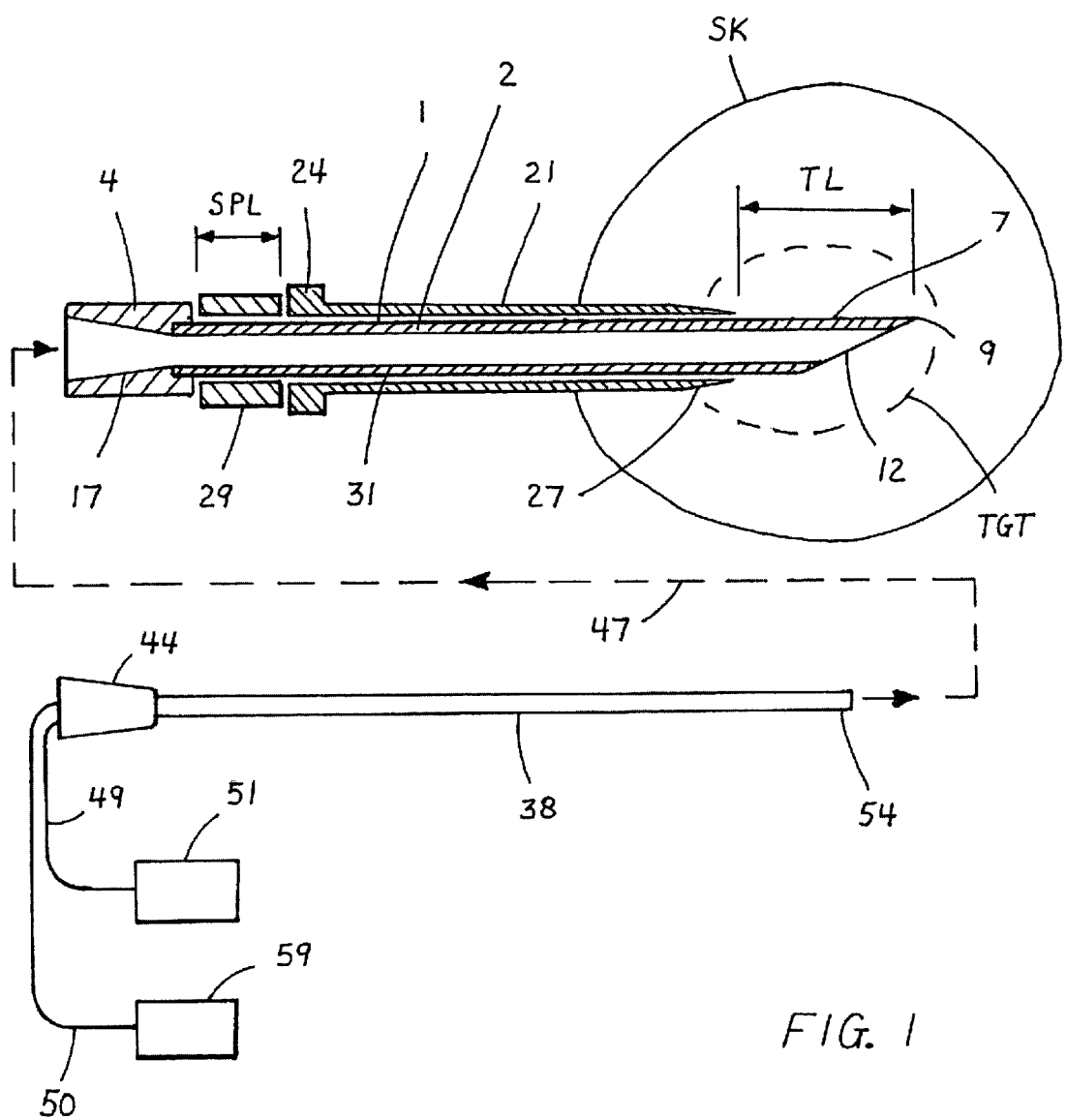
FIG. 1 is a schematic diagram showing a system with a rigid cannula, an adjustable insulating sleeve, and a spacer element.

Referring to FIG. 1, an electrode 1, shown in sectional view, includes a rigid tubing 2 that has a proximal hub 4 and a sharpened distal end. Tubing 2, for example, can be a metal tubing that is rigid. Hub 4 can be a luer tapered hub. Pointed distal tip can include a bevel 12 which has a pointed tip 9 for piercing and penetrating skin and tissue of a patient's body. In one example, tubing 2 can be a stainless steel tubing or other metal alloy tubing. In another example, the pointed distal tip can have other shapes and configurations. For example, the tip can be a trocar point, or a conical point, or be a semi-rounded or curved point. In one example, the electrode can be an over-the-wire design having a guide wire lumen through the electrode to guide along a path to the target tissue determined by a prior-positioned guide wire. The cannula 1 can be sufficiently rigid so that it can be pushed through the skin and tissue of a patient's body by a self-supported percutaneous procedure. An insulating sleeve 21 can be positioned over tubing 1 to insulate a portion of the shaft of tubing 2. In one example, the insulating sleeve can have a proximal hub or termination structure 24 to delineate its proximal end. The distal portion 27 of the insulating sleeve 21 can have a tapered configuration and a tight fit to the tubing 2. The uninsulated electrode tip portion 7 of the electrode 1 has length specified as TL. In one example, the cannula electrode 1 can be self-supportedly inserted through the skin SK of the patient's body so that the uninsulated electrode tip 7 is positioned within target tissue, the boundaries of which are indicated by the dashed line TGT. The length TL of the uninsulated electrode tip 7 can be adjusted by the clinician by moving the position of the insulating sleeve 21 on the metal tubing shaft 2. A spacer 29 can separate the hub 4 of the electrode 2 from the hub 24 of the insulating sleeve 21. In one example, the length SPL of the spacer 29 can be chosen by the clinician to give an appropriate length TL of the uninsulated electrode tip 7. In one example, prior to insertion of the electrode system into the patient's body, the clinician can decide, based on clinical evidence, the desired length of uninsulated electrode tip, and an appropriate spacer 29 can be interposed to achieve that tip exposure. One advantage is that a change in the tip exposure can be achieved using one electrode and one insulative sleeve. This can reduce complexity and expense of components in an electrode system. Another advantage is that it provides the clinician flexibility to choose the size of the exposed high frequency tip to suit the size of high frequency treatment that is desired. Another advantage is that a variety or set of spacers 29 can be provided to allow a multiplicity of selections of exposed electrode tip 7.

Referring to FIG. 1, a high frequency electrode 38 can be inserted into the electrode cannula 2 as indicated by the dashed insertion line 47. The high frequency electrode or probe 38 can have a proximal hub 44. Electrical connections within the hub can be made so that a high frequency signal output from high frequency generator can be carried by wire element 49 to the conductive shaft 38. When the shaft 38 is inserted into the cannula 1, electrical connection is made to the uninsulated electrode tip 7, thereby connecting the high frequency signal output to the exposed tip. The target tissue TGT is thus exposed to the high frequency signal output for the treatment. The connection element 49 can include temperature connections, such as thermocouple wires that connect to a thermocouple or other temperature sensor in electrode distal end 54. When electrode 38 is inserted into cannula 1, the distal tip 54 can be positioned inside the uninsulated electrode tip 7 so that temperature of the target tissue TGT can be measured during high frequency treatment. The temperature can be read out on temperature readout apparatus within the high frequency generator 51. Generator 51 can also have a reference electrode connection (not shown) that can connect to a large area ground plate attached to the patient's skin SK (also not shown) to complete the high frequency electrical circuit. In one example, electrode 38 can also have a fluid channel within it, and a fluid source 59 with flexible fluid connection 50 to enable the injection of fluid through the electrode 38 and out the distal end 54. When the electrode 38 is inserted into cannula 1 placed in the patient's body, fluid can be injected through the electrode and cannula system into the region of the target tissue TGT. This can have the advantage of enabling injection of anesthetic, contrast fluids, and other treatment augmentation agents. In one example, electrical connections 49 and fluid connection channel 50 can be flexible leader elements. In another example, these connections 49 and 50 can include intermediate connection cables and fluid connection hoses.

Referring to FIG. 1, the length of the shaft of cannula 1 can be determined to accommodate clinical needs, such as depth of target tissue from the skin. For example, in the cervical region, the tubing 2 can have a length in the range of 2 to 10 centimeters. In another example, in the thoracic or lumbar region, the tubing can be in the range of 5 to 20 centimeters or more, depending on patient anatomy. Length of exposed conductive tip 2 can be chosen according to needs. For example, in the dorsal root ganglion or cervical medial branch application in the spine, the lengths of 1 to 5 millimeters or more are appropriate. For targets in the facet joints of the lumbar spine, lengths TL of 5 to 15 millimeters are appropriate. In another example, for intra-discal therapy, the electrode can be inserted percutaneously into intravertebral discs of the patient's spine, and high frequency signal output can be applied to the intravertebral disc. In one example, tip exposures TL of 10 to 20 millimeters can be appropriate. In one example, high frequency treatment can be applied to the nerves of the spine or the intravertebral disc for the treatment of pain. In another example, cancerous tumors can be treated using high frequency signal outputs to heat the tumor target tissue. In one example, exposed tip lengths TL of 10, or 20, or 30 millimeters or more can be appropriate. In one example, the spacer 29 can be selected to accommodate the appropriate range and expected variation in length of exposed electrode tip 7. In one example, the spacer 29 can have discrete lengths in variations in 5, 10, 15 millimeters or in finer or greater variations, depending on clinical needs. In another example, the spacer 29 is not a discrete element with fixed length SPL but rather a variable length element. In one example, spacer 29 can be a variable length bushing with threaded components so that the length of the spacer SPL can be changed continuously by rotation of a screw in a threaded bushing element. In another example, the bushing 29 can be attached either to the hub 24 of the insulating sleeve or to the hub 4 of the electrode cannula and can have a threaded nut or bushing section that can provide variation of the spacing SPL of the insulative sleeve 21 with respect to the electrode cannula shaft 1. In one example, the tubing 1 can be a rigid metal tubing. The diameter of the tubing can suit the clinical application. For example, for treatment of nerves near the spinal cord, dorsal root ganglia, or medial branches of the neck, the tubing can be in the range of 0.5 millimeters or less up to 1.5 millimeters or more, depending on the size of the neural target structure. In another example for nerves in the lumbar region, the diameter of the tubing can be in the range of 1 to 2 millimeters, according to the target site. In one example, for spinal high frequency treatment of pain, the tubing can range in gauge size from 23 gauge for the smaller range to 22, 20, 19, 18, 17, or 16 gauge for larger target sites. In the example of high frequency heat ablation of cancerous tumors throughout the body, the diameter of metal tubing 2 can range from 0.5 millimeters to 3 millimeters or larger. The length of the cannula shaft 1 can vary depending on the depth of target tissue in the body. Electrodes of 1 to 5 centimeters in shaft length can be appropriate for shallow targets such as in the neck. In another example, shafts of 5 to 15 or 20 centimeters are appropriate for deeper spinal targets. In another example for tissue ablation, shafts of 100 to 400 or more millimeters are appropriate.

Figure 2:
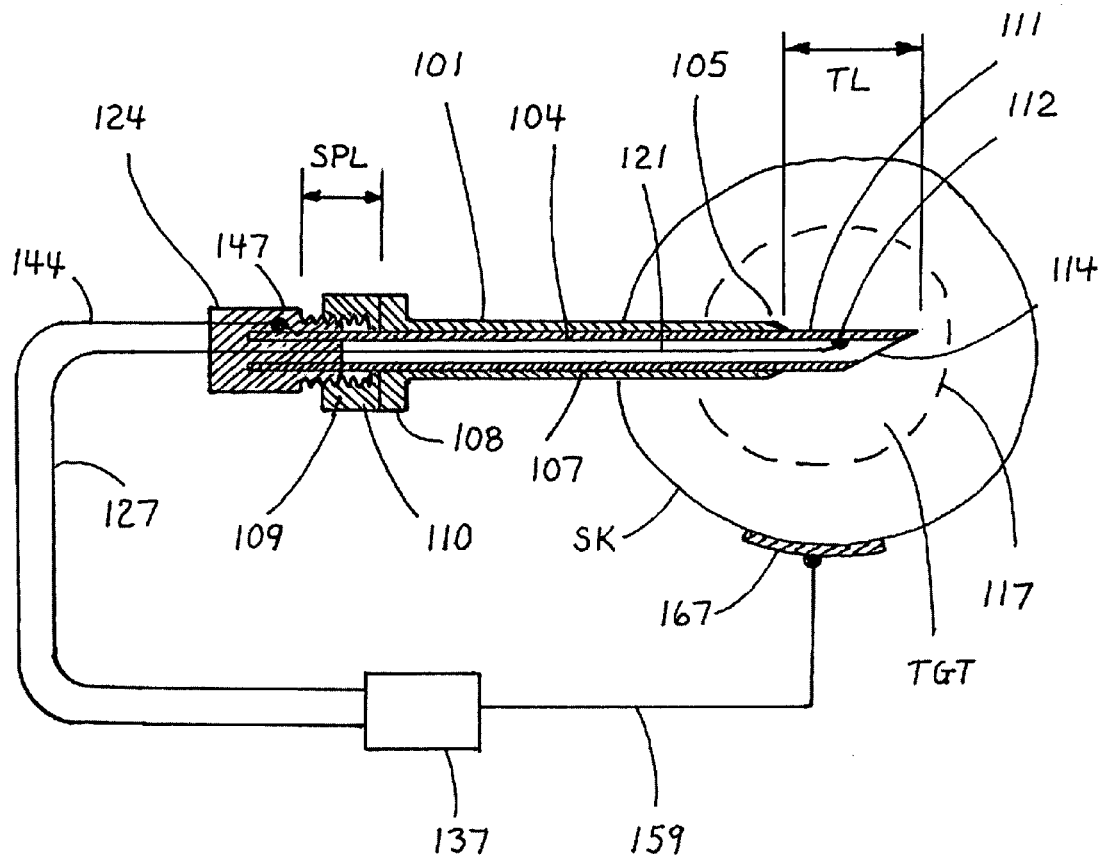
FIG. 2 is a schematic diagram showing a system with an integral high frequency electrode, adjustable insulating sleeve, and adjusting element.

Referring to FIG. 2, an integral high frequency electrode system 101 includes a longitudinally rigid tubing 104 which has exposed distal tip 111 that is sharpened to a shape 114 such as, for example, a bevel or conical or trocar point. The electrode shafts can include, for example, a metal tubing. A proximal hub 24 attaches to metal tubing 104. It has a threaded section 109 that threads into a variable spacer bushing 110. Rotating element 109 with respect to 110 changes the effective spacer length SPL. An insulative sleeve 107 slides in a close fit over metal tubing 104 to insulate a portion of the metal tubing surface. The length of the insulative sleeve 107 and its position on the tubing 104 determine the length TL of the uninsulated electrode portion 111. The distal portion 105 of the insulated sleeve can have a conical or tapered blend to the surface of the metal tubing 104. The insulative sleeve can have a proximal hub element 108. The length L of uninsulated portion 111 can be changed by changing the rotation position of hub elements 109 and 110. In this way, the spacer length SPL between the insulative sleeve hub 108 and the electrode hub 124 can be changed by the clinician at the time of treatment. A thermocouple temperature sensor 112 is positioned within the exposed tip portion 111. Temperature connection 127 connects sensor 112 to high frequency generator 137. Readout apparatus in 137 reads out the temperature at sensor 112 and thus within the target tissue TGT during treatment. Electrical connection 144 connects the high frequency signal output from the generator 137 to the electrode tubing 104 at the connection point 147. Thus the high frequency signal output from 137 can connect to the exposed tip 111, and therefore be applied to target tissue TGT. A reference connection 159 connects high frequency generator 137 to a reference electrode 167 that can be attached, for example, to the patient's skin. One advantage is that the exposed tip length TL of tip 117 can be varied or changed by the clinician before or during the procedure to suit the size of the target volume. Another advantage is that with one integral electrode and insulative sleeve, a variety of tip length exposures can be achieved. One advantage of the integral electrode system of FIG. 2 is that no insertion of probes into cannulae is required and there is one insulative sleeve element, which reduces the complexity and expense of components. As in FIG. 1, a fluid injection source and fluid conduction tubing can be inseparably integrated into the unified electrode system of FIG. 2 (not shown), further enabling injection of therapeutic or imaging fluids into target tissue TGT. One advantage of the integral electrode system and the integral adjustable bushing structure 109 and 110 is that only one spacer bushing is required, and only one electrode system and insulative sleeve is required to achieve continuous variation of tip length TL.

Figure 3:
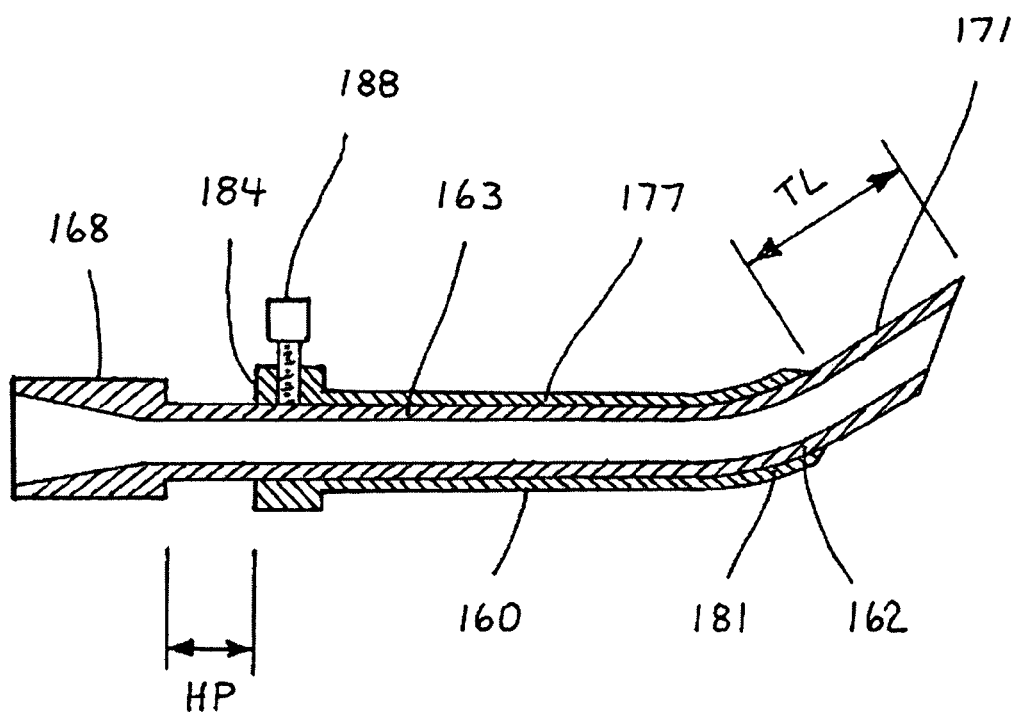
FIG. 3 is a schematic diagram showing a curved tip electrode cannula with adjustable insulating sleeve.

Referring to FIG. 3, a cannula electrode system 160 is shown in schematic sectional view. A rigid tubing 163, for example a metal tubing, has a fixed curved portion 162. An advantage of a curved tip self-supported, tissue-piercing cannula or electrode is that the curved portion can enable the steering of the electrode into the bodily tissue during insertion into a target position. Another advantage is that the curved tip portion can be used to lay proximate a target structure such as a nerve near a facet joint, thereby enabling more efficient and effective exposure to a high frequency signal output for the purpose of continuous radiofrequency or pulse radiofrequency treatment. An insulating sleeve 177 covers a portion of metal tubing 163. The insulative sleeve has a hub structure 184 with a clamping set screw 188 that can fix the position of the insulative sleeve 177 with respect to metal tubing shaft 163. The adjustment of the length of the exposed conductive tip 171, represented by length TL, can be adjusted by the clinician to suit clinical needs. The length TL can correspond to the length of the curved segment of the exposed electrode tip. The insulative sleeve 177 can be made of a semi-rigid or longitudinally rigid, flexible plastic insulation such as Teflon or other plastics so that the insulative sleeve can slide and curve along with the curvature of the distal tip of the metal tubing 162. For example, the insulative sleeve is curving on the curvilinear portion of the metal tubing as shown by the distal portion 181 of the insulative sleeve 177. The metal tubing 163 has a hub structure 168. In one example, the hub can be a luer hub. According to the position of the insulative sleeve 163 that is controlled by the clamping hub 184 relative to metal tubing 163, the relative hub position distance HP can be changed by the clinician. In this way, the length of exposed tip TL can also be changed accordingly. One advantage is that the clinician can determine prior to or during the procedure the desired tip length TL and accordingly establish that tip length by adjustment of the hub position HP, and clamp that position by clamping device such as set screw 188 on hub 184. In another example, an integral electrode with a curved tip analogous to the one shown in FIG. 2 and described in U.S. patent application Ser. No. 11/355,960 entitled "Integral High Frequency Electrode" can have an adjustable insulative sleeve, as shown in FIG. 3. Various embodiments and implementations of an integral electrode with rigid curved tip and flexible, curvable insulation sleeve are possible using the designs of the above-cited patent application together with the embodiments shown herein.

Figure 4:
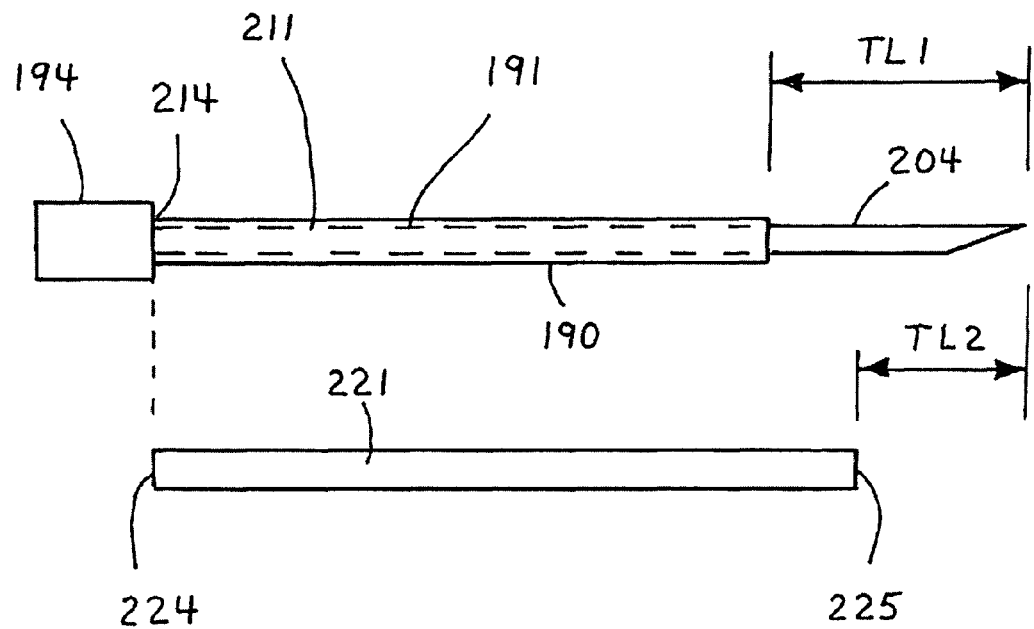
FIG. 4 is a schematic diagram showing a system of an electrode with insulative sleeves of differing insulation lengths.

Referring to FIG. 4, a rigid cannula or electrode system 190 is shown in schematic side elevation view. A metal tubing 191 is insulated by an insulating sleeve 211. The metal tubing 191 has connection hub 194, and the insulative sleeve 111 has proximal end that proximates or abuts the hub 194. The length of the insulating sleeve 211 relative to the length of the electrode shaft 191 determines the length TL1 of the uninsulated electrode tip 204. For a given or fixed length of insulating sleeve 211, the tip length TL1 is determined. Also shown is a second insulative sleeve 221 which has a different length from its proximal end 224 to its distal end 225. The insulating sleeve 211 can be removed from electrode shaft 191 and the other insulating sleeve 221 can be slid over the shaft so that proximal end 224 abuts the hub element 194. Thus, a different uninsulated electrode tip length TL2 can be achieved. Various lengths of discrete insulative tubing such as 211 and 221 can be supplied with the electrode cannula 191 to provide differences in desired tip exposure. For example, if tip exposures of 2, 5, 10, 15, or 20 millimeters are desired, then insulative sleeves, such as 211, of different lengths to provide those uninsulated tip exposures can be provided with the electrode or cannula 191. The length of the insulative sleeve can be chosen by the clinician at the time of procedure. In another example, an insulative sleeve 211 can be provided with electrode or cannula 191 such that the initial tip exposure TL1 is minimal. The clinician can then cut the length of the insulative sleeve 211 so as to achieve the desired tip exposure length TL1 according to clinical needs. One advantage is that one cannula or electrode together with one or a discrete number of insulative sleeves can be supplied to achieve a variety of electrode tip lengths. This simplifies and makes less expensive the equipment needed to achieve a variety of clinical objectives. As in the other embodiments shown in the other figures, the cannula or electrode 191 can take various forms. In one example, element 191 can be a metal cannula with hub, such as a luer hub, into which a high frequency electrode with thermal sensor can be inserted, as for example in FIG. 1. In another example, element 191 can be an integral high frequency electrode that comprises a temperature sensor, high frequency electrode connection, and a fluid injection port and conduit structure. The element 191 in the examples herein, can have varying distal tip shapes including conically pointed tips, closed metal tips, open ground bevel points, metal tubing, fully rounded and smooth distal tips, and other shapes according to the target structure and penetration needs of the electrode or cannula system.

Figure 5:
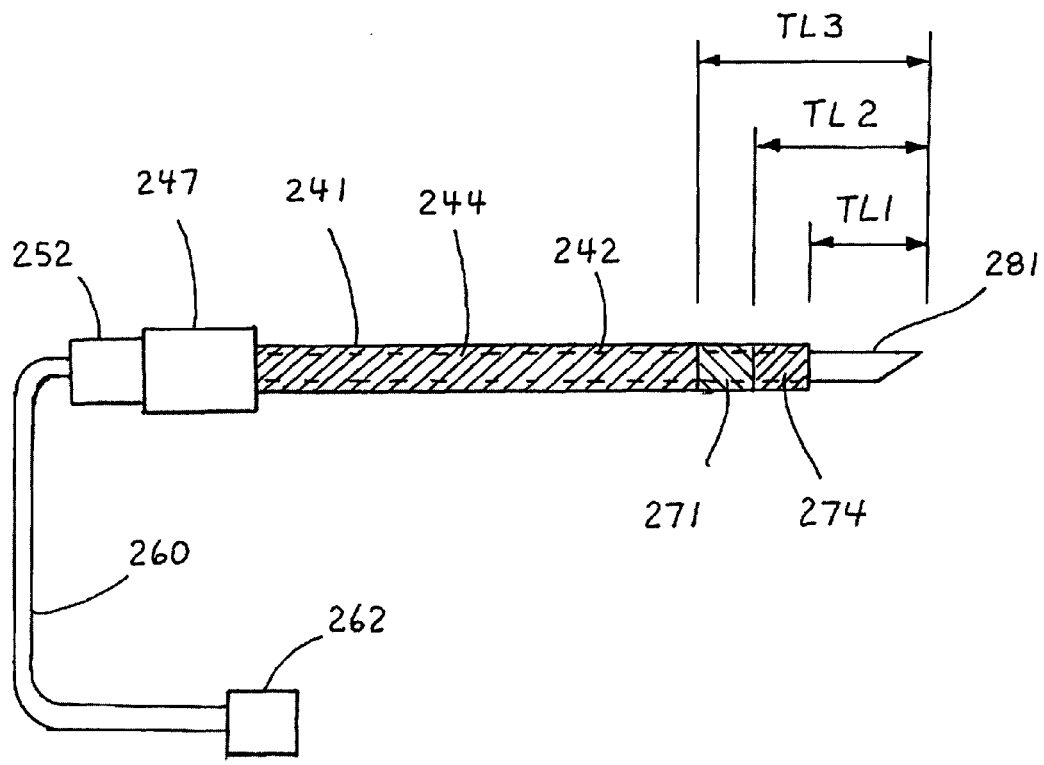
FIG. 5 is a schematic diagram showing an electrode system having insulation with removable sections.

Referring to FIG. 5, a high frequency electrode system 241 is schematically shown from a side elevation view. An underlying rigid shaft 242 is insulated over a portion of its surface by insulation 244. An uninsulated distal electrode tip 281, in one configuration, has exposed length TL1. The insulation has band structures illustrated by the portions 271 and 274 that are shaded. The insulating bands can be peeled off or cut off of the underlying shafts 241 to expose greater amounts of uninsulated electrode tip portion 281. For example, if band 274, which is indicated by a shaded region, is removed, then the uninsulated electrode tip 281 will have an exposed conductive tip length of TL2. In another example, if both the insulated bands 271 and 274 are removed from the underlying electrode shaft 242, then the exposed electrode tip 281 will have a conductive exposed tip length of TL3. A multiplicity of such removable insulative sections can be incorporated into the electrode system 241, enabling the clinician to change the uninsulated electrode tip length prior to surgery, depending on the clinical needs. In one example, the insulative sleeve 244 can be made of Teflon of a particular color, for example black. The other insulative bands, such as 271 and 274, can also be made of Teflon and be of different colors, such as white and yellow. Thus the clinician can easily see the position of the bands, and can see that the bands are in place or have been removed. The lengths of the bands can be of a desired discrete length, such as 5 millimeters. In one example, the length of the exposed conductive tip 281 can be enlarged by 5 millimeter increments by removing one, two, or more such insulative bands from the proximal end of the electrode 241. The insulative material such as 244 can be made of a heat shrink plastic material such as Teflon, poluethylene, polyurathene, or other dielectric insulative materials. Such material can be secured strongly to the underlying tubing 241. However, the surgeon can nick or cut an insulative band at a desired position and easily remove it by tweezers prior to surgery without compromising the integrity of the rest of the insulation or insulating bands. An advantage is that the surgeon can change the degree of insulation on the electrode easily prior to surgery. Another advantage is that the electrode has only one element with fixed insulation already in place. This reduces the complexity of components and simplifies the inventorying and reduces the cost of the electrode system.

Figure 6:
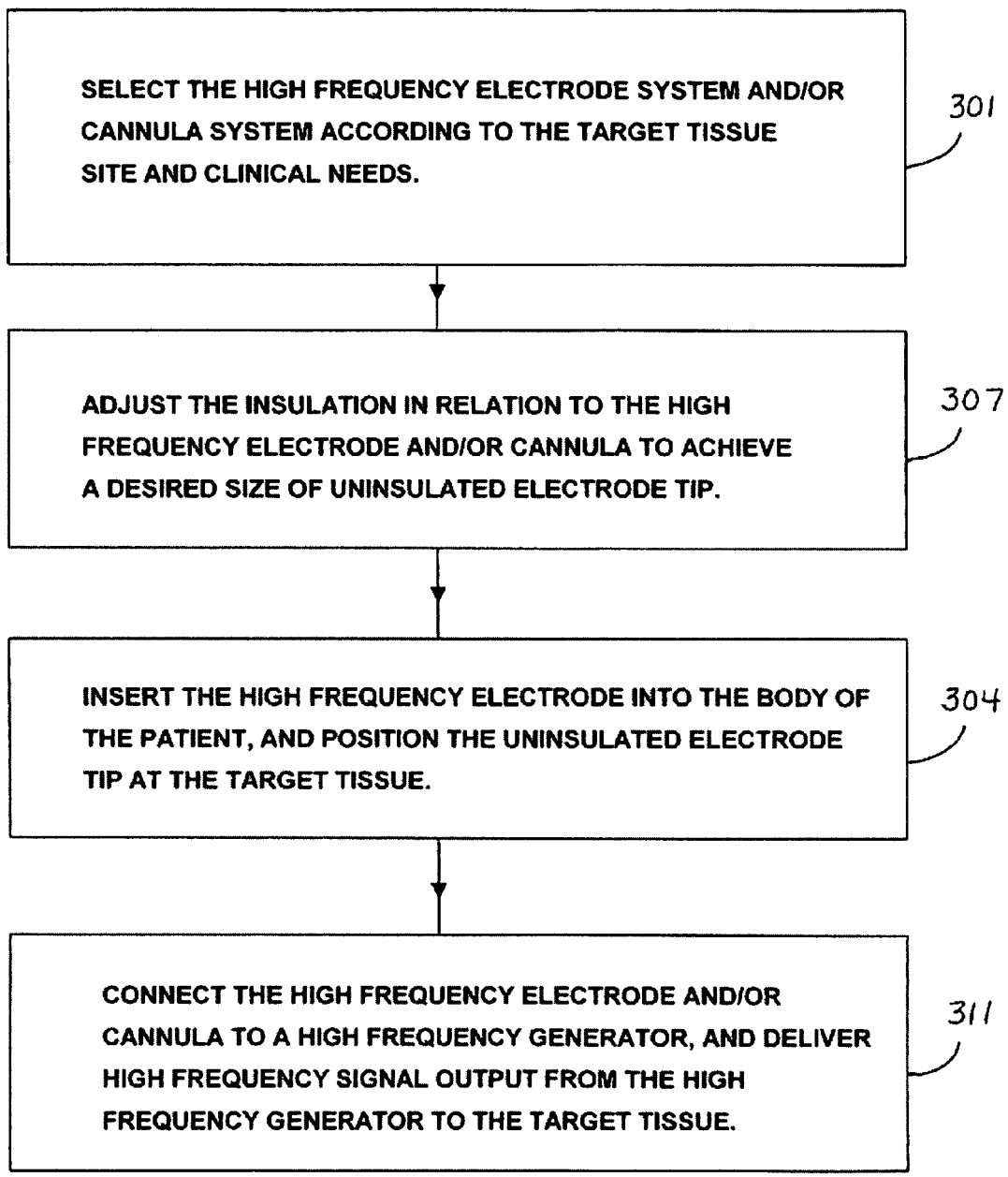
FIG. 6 shows a process for application of a system comprising an adjustable electrode system.

Referring to FIG. 6, a process is shown that includes a step 301 in which a high frequency electrode system and/or cannula system is selected according to the nature and geometry of the tissue and treatment that the clinician desires. In step 307, the degree of exposure of the exposed conductive tip on the electrode is adjusted by adjustment of the insulation on the electrode. This includes adjusting the exposed electrode tip length to achieve the desired size of tip exposure according to the geometry of the target tissue and the level of high frequency therapy desired by the clinician. Step 307 can include, for example: insertion of a spacing bushing at the electrode and insulation hubs, adjustment of a variable spacing or clamping system at the hub structure of the electrode or cannula, selection of a desired length of insulation sleeve, removal of one or more insulation sections from the insulative sleeve, cutting an insulation sleeve according to a desired length of tip exposure, and other implementations related to adjustment or modification of an insulative sleeve with respect to an electrode shaft. In block 304, the high frequency electrode system is inserted into the patient's bodily tissue so that the uninsulated electrode tip is positioned at a desired target tissue. Step 311 comprises connecting the high frequency electrode and/or cannula to a high frequency generator and delivering the high frequency signal output from the high frequency generator through the electrode system to the target tissue to achieve the desired high frequency therapy. This step can, for example, include the connection of the electrode to a radiofrequency (rf) generator system and delivering either continuous rf signal output or pulsed rf signal output through the electrode to a target tissue.

A number of embodiments of the invention have been described. Nevertheless, it will be understood that various modifications may be made without departing from the spirit and scope of the invention. Accordingly, other embodiments are within the scope of the following claims:

What is claimed is:

1. An adjustable high frequency electrode system comprising:
   a rigid shaft adapted to be inserted into a target tissue of a living body, the rigid shaft having a distal end and a proximal end, the distal end comprising an uninsulated electrode tip;
   an insulating covering with a proximal end and a distal end that covers at least a portion of the rigid shaft and at least a portion of the insulating covering can be moved with respect to the rigid shaft so that the exposed surface of the uninsulated electrode tip can be adjusted;
   the electrode system being configured to be connected to a high frequency generator so that a high frequency signal output from the high frequency generator can be applied to the target tissue near the uninsulated electrode tip when the rigid shaft is inserted into the living body; and a spacer between and directly adjacent to a hub of the electrode tip and a hub of the insulating covering, wherein the spacer includes a distal end, a proximal end, and a length between the distal and proximal end of the spacer, wherein the length of the spacer determines the length of the uninsulated electrode tip.

2. The system of claim 1, wherein the rigid shaft comprises a metal tubing, and the uninsulated electrode tip comprises at least a portion of a distal end of the metal tubing.

3. The system of claim 2, wherein the metal tubing has a sharpened tip at the distal end of the metal tubing to enable penetration of the tissue of the living body.

4. The system of claim 2, wherein the distal end of the metal tubing has a curve shape.

5. The system of claim 2, wherein the insulating covering comprises an insulating sleeve of electrically insulating material that covers at least a portion of the rigid shaft, and at least a portion of the insulating sleeve can be moved with respect to the rigid shaft to adjust the length of the uninsulated electrode tip.

6. The system of claim 5, further comprising a fixation clamp that enables the insulating sleeve to be fixed at adjusted positions on the metal tubing.

7. The system of claim 1, wherein the insulating covering comprises a removable insulative member covering at least a portion of the distal end.

8. The system of claim 1, wherein the rigid shaft comprises a metal tubing and the uninsulated electrode tip comprises a portion of a distal end of the metal tubing, and the insulating covering comprises an insulating sleeve of insulating material that can be moved on the metal tubing to adjust the length of the uninsulated electrode tip.

9. The system of claim 1, wherein the rigid shaft comprises a metal tubing and the uninsulated electrode tip comprises a portion of the distal end of the metal tubing, and the insulating covering comprises a removable insulating member covering at least a portion of the distal end of the metal tubing.

10. A method of treating target tissue in the living body comprising:
determining the size of a high frequency electrode needed to treat the target tissue with a high frequency signal output;
selecting a high frequency electrode system having a rigid shaft adapted to be inserted into the target tissue, the distal end comprising an uninsulated electrode tip, and an insulating covering that covers at least a portion of the rigid shaft and at least a portion of the insulating covering can be moved with respect to the rigid shaft so that an exposed surface of the uninsulated electrode tip can be adjusted, wherein the electrode system is configured to be connected to a high frequency generator so that the high frequency signal output from the high frequency generator can be applied to a target tissue near the uninsulated electrode tip when the rigid shaft is inserted into a living body;
selecting a spacer according to the uninsulated electrode tip length;
adjusting the exposed surface according to the size of high frequency electrode;

interposing a spacer between and directly adjacent to a hub of the electrode tip and a hub of the insulating covering; and connecting the high frequency electrode system to a high frequency generator to deliver a high frequency signal output to the target tissue through the uninsulated electrode tip.

11. The system of claim 1, wherein the proximal end of the rigid shaft comprises the hub of the electrode tip.

12. The system of claim 1, wherein the proximal end of the insulating covering comprises the hub of the insulating covering.

13. An adjustable high frequency electrode system comprising:
a rigid shaft adapted to be inserted into a target tissue of a living body, the rigid shaft having a distal end and a proximal end, the distal end comprising an uninsulated electrode tip;
an insulating covering with a proximal end and a distal end that covers at least a portion of the rigid shaft and at least a portion of the insulating covering can be moved with respect to the rigid shaft so that the exposed surface of the uninsulated electrode tip can be adjusted;
the electrode system being configured to be connected to a high frequency generator so that a high frequency signal output from the high frequency generator can be applied to the target tissue near the uninsulated electrode tip when the rigid shaft is inserted into the living body; and
a set of spacers including spacers of discrete lengths, wherein one or more spacers can be interposed between a hub of the electrode tip and a hub of the insulating covering, and wherein the one or more spacers determines the length of the uninsulated electrode tip.

14. A method of treating target tissue in the living body comprising:
determining the size of a high frequency electrode needed to treat the target tissue with a high frequency signal output;
selecting a high frequency electrode system having a rigid shaft adapted to be inserted into the target tissue, the distal end comprising an uninsulated electrode tip, and an insulating covering that covers at least a portion of the rigid shaft and at least a portion of the insulating covering can be moved with respect to the rigid shaft so that an exposed surface of the uninsulated electrode tip can be adjusted, wherein the electrode system is configured to be connected to a high frequency generator so that the high frequency signal output from the high frequency generator can be applied to a target tissue near the uninsulated electrode tip when the rigid shaft is inserted into a living body;
selecting one or more spacers from a set of spacers according to the uninsulated electrode tip length, wherein the set of spacers includes spacers of discrete lengths;
adjusting the exposed surface according to the size of high frequency electrode; and
connecting the high frequency electrode system to a high frequency generator to deliver a high frequency signal output to the target tissue through the uninsulated electrode tip.

* * * * *